(12) United States Patent
Ami et al.

(10) Patent No.: US 11,284,835 B2
(45) Date of Patent: Mar. 29, 2022

(54) METHOD FOR ASSESSING PAIN CAUSED BY ADMINISTRATION OF DRUG SOLUTION, AND METHOD FOR SELECTING DRUG SOLUTION ADMINISTRATION

(71) Applicant: TERUMO KABUSHIKI KAISHA, Tokyo (JP)

(72) Inventors: Nozomi Ami, Kanagawa (JP); Shigeru Tamatsukuri, Tokyo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 414 days.

(21) Appl. No.: 16/119,912

(22) Filed: Aug. 31, 2018

(65) Prior Publication Data

US 2018/0368760 A1    Dec. 27, 2018

Related U.S. Application Data

(63) Continuation of application No. PCT/JP2016/056741, filed on Mar. 4, 2016.

(51) Int. Cl.
*A61B 5/00* (2006.01)
*A61K 49/00* (2006.01)
(Continued)

(52) U.S. Cl.
CPC ............ *A61B 5/4824* (2013.01); *A61B 5/296* (2021.01); *A61B 5/389* (2021.01); *A61B 5/4848* (2013.01); *A61B 5/6838* (2013.01); *A61B 5/6846* (2013.01); *A61K 9/0019* (2013.01); *A61K 49/0008* (2013.01); *G01N 33/483* (2013.01); *A61B 5/6884* (2013.01);
(Continued)

(58) Field of Classification Search
None
See application file for complete search history.

(56) References Cited

FOREIGN PATENT DOCUMENTS

WO    WO-2013/141351 A1    9/2013

OTHER PUBLICATIONS

Okamoto et al., 2012 K. Okamoto, N. Ami, H. Oshima Assessment of needle insertion pain with flexor reflex responses in anesthetized rats Pain Res., 27 (2012), pp. 215-225 (Year: 2012).*

(Continued)

*Primary Examiner* — Sean P Dougherty
*Assistant Examiner* — Benjamin S Melhus
(74) *Attorney, Agent, or Firm* — Foley & Lardner LLP

(57) ABSTRACT

A method for assessing pain caused by administration of a drug solution includes: anesthetizing an experimental animal; inserting a measurement electrode into skeletal muscle of the anesthetized experimental animal; puncturing an injection needle into a predetermined part of the anesthetized experimental animal while measuring a myoelectric potential of the skeletal muscle with the measurement electrode; administering a drug solution to the anesthetized experimental animal; and (i) measuring a duration time of the myoelectric response caused by the administration of the drug solution, and/or (ii) measuring an EMG intensity obtained by integrating absolute values of myoelectric potentials during a period from occurrence of the myoelectric response by the administration of the drug solution to disappearance of the myoelectric response.

17 Claims, 10 Drawing Sheets

(51) Int. Cl.
   *A61K 9/00*    (2006.01)
   *A61B 5/0492*  (2006.01)
   *G01N 33/483*  (2006.01)
   *A61B 5/296*   (2021.01)
   *A61B 5/389*   (2021.01)
   *A61D 7/04*    (2006.01)

(52) U.S. Cl.
   CPC ....... *A61B 2503/40* (2013.01); *A61B 2503/42* (2013.01); *A61D 7/04* (2013.01)

(56) References Cited

OTHER PUBLICATIONS

Ando, R., Watanabe, C., Characteristics of propofol-evoked vascular pain in anaesthetized rats, Br. J. Anaesth., 95 ( 2005 ) 384-392. (Year: 2005).*

International Search Report with English language translation and Written Opinion issued in International Application No. PCT/JP2016/056741 dated May 10, 2016.

Masumi, et al., "Nitric oxide involvement in lipid emulsion-induced vascular pain in anesthetized rats", European Journal of Pharmacology 594: 64-69 (2008).

Invitation to Respond to Written Opinion, dated Jul. 1, 2021, issued in corresponding Singaporean Patent Application No. 11201807578U (7 pages).

* cited by examiner

Jørgensen JT et al;Ann Pharmacother 30:729-732,1996

Ugawa, S et al: J Clin Invest 110:1185-1190, 2002

Henderson LA et al;Pain 120:286-296,2006

Gazerani P et al:Pain 124:338-348, 2006

METHOD FOR ASSESSING PAIN CAUSED BY ADMINISTRATION OF DRUG SOLUTION, AND METHOD FOR SELECTING DRUG SOLUTION ADMINISTRATION

CROSS-REFERENCE TO RELATED APPLICATION

This application is a bypass continuation of PCT Application No. PCT/JP2016/056741, filed on Mar. 4, 2016, the contents of which are hereby incorporated by reference in their entirety.

BACKGROUND

The present disclosure relates to a method for assessing pain caused by administration of a drug solution and a method for selecting drug solution administration.

An injection is a drug solution administration method that is widely used, but pain caused by the injection is unpleasant for a patient. Thus, it is desired to reduce the pain caused by the injection. The pain caused by the injection includes pain caused by puncture of an injection needle and pain caused by a drug solution (infusion of the drug solution). Therefore, it is necessary to make it possible to assess (quantify) each of the pain caused by the puncture and the pain caused by the administration of the drug solution in order to reduce the pain caused by the injection.

In relation to this assessment, a method for assessing pain caused by puncture of a needle in a spinal reflex of anesthetized rats has been proposed in Okamoto, K., Ami, N., Oshima, H., "Assessment of needle insertion pain with flexor reflex responses in anesthetized rats", Pain Research, The Japanese Association for Study of Pain, 2012, Vol. 27, No. 24, p. 215-225 ("Okamoto").

In addition, a method for assessing vascular pain from an electromyogram (EMG) has been proposed in Masumi, S, Senba, E, "Nitric oxide involvement in lipid emulsion-induced vascular pain in anesthetized rats", Eur J Pharmacol, Elsevier, 2008, No. 594, pp. 64-69 ("Masumi").

SUMMARY

However, conventionally, there has been no proposal for an effective method for assessing (quantifying) the pain caused by the administration of a drug solution.

Embodiments described herein have been developed in consideration of such a problem, and an object thereof is to provide a method for assessing pain caused by administration of a drug solution and a method for selecting drug solution administration.

According to one embodiment, a method for assessing pain by administration of a drug solution includes: preparing a mammalian experimental animal having a predetermined part of a body and a skeletal muscle bent by a spinal reflex when a stimulus is applied to the predetermined part; anesthetizing the experimental animal by inhalation anesthesia; inserting a measurement electrode into the skeletal muscle of the anesthetized experimental animal; puncturing an injection needle into the predetermined part of the anesthetized experimental animal while measuring a myoelectric potential of the skeletal muscle by the measurement electrode; administering a drug solution to the anesthetized experimental animal through the injection needle after a myoelectric response caused by the puncture of the injection needle disappears; and performing at least one of measurement of a duration time of the myoelectric response caused by the administration of the drug solution and measurement of an EMG intensity obtained by integrating absolute values of myoelectric potentials during the period from the occurrence of the myoelectric response by the administration of the drug solution to the disappearance of the myoelectric response.

According to the method described above, the drug solution is administered to the experimental animal and the myoelectric response caused by the administration of the drug solution is measured after the myoelectric response caused by the puncture of the injection needle disappears, and thus, the myoelectric response caused by the puncture and the myoelectric response caused by the drug solution administration do not overlap each other on the electromyogram (EMG). In this manner, it is possible to assess (quantify) the pain caused by the administration of the drug solution separately from the pain caused by the puncture. In addition, the pain sensed by a human indicates the same tendency as a result of the myoelectric response using the experimental animal, and thus, it is possible to assess the pain caused by the drug solution administration at the time of the injection into the human according to the method of the present invention. Therefore, it is possible to contribute to development of drug solution injection for humans with reduced pain according to the method of the present invention.

In the above-described method for assessing pain caused by administration of a drug solution, a plurality of the drug solutions having different compositions may be administered to a plurality of administration sites of the predetermined part of the experimental animal under an identical administration condition or the drug solution having an identical composition is administered to a plurality of administration sites of the predetermined part of the experimental animal under different administration conditions.

Thus, with the administration to the plurality of sites of the same experimental animal, it is possible to compare differences in pain depending on the drug solution composition or the administration condition, and to select a drug solution or an administration condition accompanied by less pain.

In the above-described method for assessing pain caused by administration of a drug solution, the experimental animal may be a rat.

In the above-described method for assessing pain caused by administration of a drug solution, the predetermined part may be a plantar subcutaneous, and the skeletal muscle may be a semitendinosus muscle.

In the above-described method for assessing pain caused by administration of a drug solution, a dose per site at the plurality of administration sites may be a range of 10 to 100 μL.

In the above-described method for assessing pain caused by administration of a drug solution, an interval between adjacent administration sites may be 2 mm or more.

As a result, it is possible to avoid influence by the adjacent administration site when acquiring the myoelectric response caused by the drug solution administration and to perform highly accurate measurement.

In the above-described method for assessing pain caused by administration of a drug solution, a total dose at the plurality of administration sites may be 200 μL or less.

In the above-described method for assessing pain caused by administration of a drug solution, an administration rate of the drug solution may be a range of 5 to 100 μL/sec.

In the above-described method for assessing pain caused by administration of a drug solution, the administration of the drug solution may be started after a lapse of one second or more since the myoelectric response caused by the puncture has disappeared.

As a result, it is possible to more effectively measure the myoelectric response caused by the drug solution administration separately from the myoelectric response caused by the puncture.

In the above-described method for assessing pain caused by administration of a drug solution, the drug solution may be administered only when the myoelectric response caused by the puncture occurs.

As a result, it is possible to avoid wasteful drug solution administration.

In the above-described method for assessing pain caused by administration of a drug solution, a bipolar electrode may be used as the measurement electrode and a reference electrode may be pasted to the thoracic skin surface of the experimental animal.

As a result, it is possible to acquire a waveform of the myoelectric potential with less noise and to improve measurement accuracy.

In another embodiment, a method for selecting drug solution administration includes: a preparation step of preparing a mammalian experimental animal having a predetermined part of a body and a skeletal muscle bent by a spinal reflex when a stimulus is applied to the predetermined part; an anesthesia step of anesthetizing the experimental animal by inhalation anesthesia; a measurement electrode placement step of placing a measurement electrode in the skeletal muscle of the anesthetized experimental animal; a puncture step of inserting an injection needle into the predetermined part of the anesthetized experimental animal while measuring a myoelectric potential of the skeletal muscle by the measurement electrode; an administration step of administering a drug solution to the anesthetized experimental animal through the injection needle after a myoelectric response caused by the puncture of the injection needle disappears; and a measurement step of performing at least one of measurement of an EMG intensity obtained by integrating absolute values of the myoelectric potential from occurrence to disappearance of the myoelectric response caused by the administration of the drug solution and measurement of a duration time of the myoelectric response caused by the administration of the drug solution. The puncture step, the administration step, and the measurement step are performed for each of a plurality of drug solutions having different compositions or for each of a plurality of administration conditions. The method further includes a identifying step of identifying a drug solution composition with which the duration time is shortest or the EMG intensity is smallest among the plurality of drug solutions having different compositions, or identifying an administration condition with which the duration time is shortest or the EMG intensity is smallest, among the plurality of administration conditions.

According to this method, it is possible to select the drug solution composition or the administration condition accompanied by less pain.

According to the method for assessing pain caused by administration of a drug solution described above, it is possible to assess (quantify) the pain caused by the administration of the drug solution separately from the pain caused by the puncture. Further, according to the method for selecting drug solution administration described above, it is possible to select the drug solution composition or the administration condition accompanied by less pain.

DETAILED DESCRIPTION

Hereinafter, embodiments of a method for assessing pain caused by administration of a drug solution and a method for selecting drug solution administration will be described with reference to the accompanying drawings.

Figure 1:
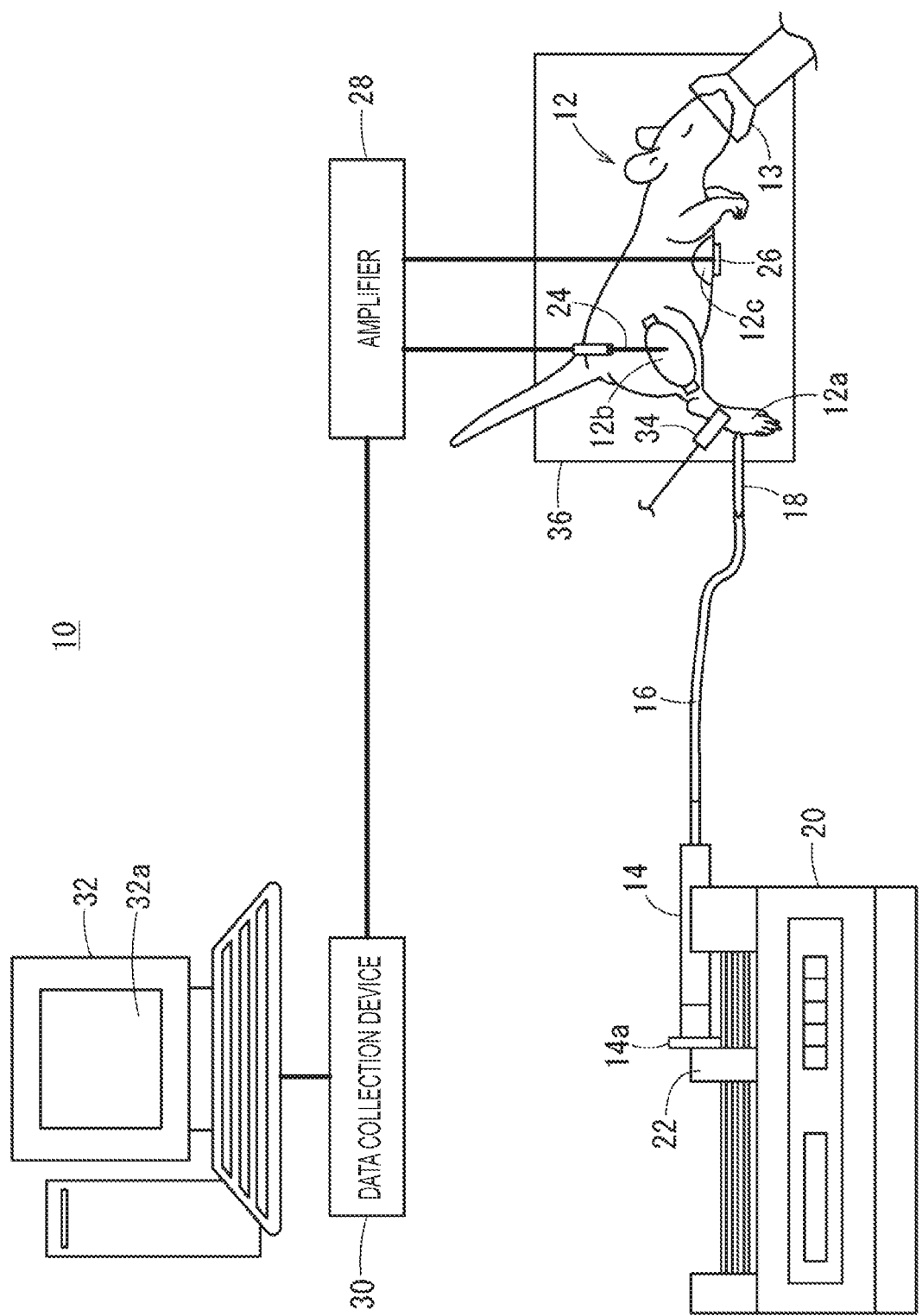
FIG. 1 is a schematic diagram of a measurement system according to one configuration example used in a method of the present invention.

FIG. 1 is a schematic diagram of a measurement system 10 according to one example configuration used in the methods described herein. In the embodiment illustrated in FIG. 1, a subject (experimental animal) used for assessment of pain caused by administration of a drug solution is a rat 12. Conditions of the rat 12 that can be used are, for example, an age in range of 7 to 10 weeks old, a body weight in a range of 200 to 400 g, and a strain that is SD (other strains are also possible). An acclimation and quarantine period of the rat 12 is preferably five days or longer. An anesthesia mask 13 is attached to the rat 12, and inhalation anesthesia is performed.

Incidentally, the experimental animal that can be used may be any mammal having a predetermined part of a body and a skeletal muscle to be bent by reflection of a spinal reflex when a stimulus is applied to the predetermined part. In the case of the rat 12, a semitendinosus muscle 12b is bent by the spinal reflex when a stimulus is applied to a plantar subcutaneous 12a. Examples of the experimental animal of the mammal that can be used other than the rat 12 include a mouse, a guinea pig, a gerbil, a hamster, a ferret, a rabbit, a dog, a minipig, and the like.

The drug solution is filled in a syringe 14. The capacity of the syringe 14 is a range of, for example, 1 to 10 mL. The syringe 14 is connected to an injection needle 18 through a soft tube 16 made of a resin. A size of the applicable injection needle 18 is a range of, for example, 34 G to 22 G. The injection needle 18 is punctured under the plantar subcutaneous 12a of the rat 12.

The syringe 14 is attached to a syringe pump 20. The syringe pump 20 includes a slider 22 that pushes a pusher 14a of the attached syringe 14. In the syringe pump 20, the speed at which the pusher 14a is pushed by the slider 22 is determined based on a set feeding amount and a type (capacity) of the syringe 14. As a result, an administration rate of the drug solution to the rat 12 can be arbitrarily set. The administration rate of the drug solution is a range of, for example, 5 to 100 µL/sec.

In order to measure the pain caused by the administration of the drug solution, a myoelectric potential of the semitendinosus muscle 12b of the thigh of the rat 12 is recorded. At the time of recording the myoelectric potential, a needle-shaped measurement electrode 24 (for example, a bipolar hook electrode) is punctured under the semitendinosus muscle 12b to be placed, and a reference electrode 26 is pasted to a thoracic skin surface 12c. Potential signals from the measurement electrode 24 and the reference electrode 26 are amplified by a high-sensitivity bioelectric amplifier 28 and transmitted to a data collection device 30.

In the data collection device 30, data (potential signal) is recorded at a predetermined sampling interval (for example, 0.1 ms) to generate a myoelectric potential waveform. The myoelectric potential waveform generated by the data collection device 30 is displayed on a monitor screen 32a of a personal computer 32.

In addition, as pre-preparation for measuring the myoelectric response caused by injection, electrical stimulation using a clip-type stimulating electrode 34 is performed in order to control an anesthetic depth that enables measurement of the myoelectric response (muscle contraction) in this measurement system 10. The clip-type stimulating electrode 34 is connected to an electrostimulator (not illustrated).

The method for assessing pain caused by administration of a drug solution and the method for selecting drug solution administration can be performed, for example, as follows when using the measurement system 10 configured as described above.

When it is desired to investigate which composition causes the least pain among a plurality of different drug solution compositions, a plurality of drug solutions having different compositions is prepared. A difference in drug solution composition depends on, for example, a type of a drug solution component (for example, a chemical structure of an active component, a buffer, a stabilizer, an antioxidant, or the like), a pH value, a viscosity, and the like. Alternatively, when it is desired to investigate which administration condition causes the least pain among a plurality of different drug administration conditions, a plurality of different administration conditions is prepared for a drug solution having the same composition. Parameters of the administration condition include an administration rate (infusion rate) of a drug solution and a dose.

A rat 12 serving as a subject is prepared (a preparation step), and the rat 12 is subjected to inhalation anesthesia (an anesthesia step). Examples of an applicable inhalation anesthetic include isoflurane. An anesthetic concentration with respect to air is a range of, for example, 3 to 4%/Air at the time of introduction of anesthesia and a range of, for example, 1 to 2%/Air at the time of recording. Incidentally, it is preferable to heat the rat 12 with a warming mat to keep the body temperature constant during the anesthesia.

Next, the measurement electrode 24 is placed in the semitendinosus muscle 12b of the anesthetized rat 12 (a measurement electrode placement step). Specifically, the clip-type stimulating electrode 34 is used to clamp the dorsum and sole of the hind paw of the rat 12, and an electrical stimulus (for example, 40 Hz, 10 mA, 2 ms) is applied to C fibers of pain sensation via the clip-type stimulating electrode 34 by the electrostimulator (not illustrated). At this time, the thigh skin at a position where contraction has been recognized is incised by about 1 cm to expose the semitendinosus muscle 12b, and then, the measurement electrode 24 is inserted.

When the measurement electrode 24 is placed, an electrical stimulus (for example, 40 Hz, 5 mA, 2 ms) is applied again by the electrostimulator (not illustrated) via the clip-type stimulating electrode 34, and the anesthetic depth of the rat 12 is finely adjusted while referring to the myoelectric response intensity. Thereafter, the anesthetic depth is kept constant.

In addition, the thorax of the rat 12 is depilated to expose the thoracic skin 12c, and then, the reference electrode 26 is pasted to the thoracic skin surface 12c. Incidentally, the reference electrode 26 may be pasted before, after, or in parallel with the placement of the measurement electrode 24. When a bipolar electrode is used as the measurement electrode 24 and the reference electrode 26 is pasted to the thoracic skin surface 12c of the rat 12, it is possible to acquire the myoelectric potential waveform with less noise and to improve the measurement accuracy. Incidentally, the measurement electrode 24 may be a monopolar electrode when the reference electrode 26 is pasted.

Once the above preparation has been completed, a puncture step, an administration step, and a measurement step to be described below are performed for each of the plurality of drug solutions having different compositions or for each of the plurality of administration conditions using the same rat 12. That is, the puncture step, the administration step, and the measurement step are performed with a certain drug solution composition or administration condition, and then, the puncture step, the administration step, and the measurement step are repeatedly performed with different drug solution compositions or administration conditions using the same rat 12.

In the puncture step, the injection needle 18 is punctured under the plantar subcutaneous 12*a* of the anesthetized rat 12. In this case, when the entire blade surface provided at a distal end of the injection needle 18 pierces the plantar subcutaneous 12*a*, the puncture is completed. When the injection needle 18 is punctured under the rat 12 in this manner, a myoelectric response caused by puncture occurs.

In the administration step following the puncture step, a drug solution is administered to the anesthetized rat 12 through the injection needle 18 after the myoelectric response caused by puncture of the injection needle 18 disappears. In this case, the syringe pump 20 pushes the pusher 14*a* of the syringe 14 based on the preset administration rate and dose so that the drug solution is infused into the plantar subcutaneous 12*a* of the rat 12 at the set administration rate and dose.

Incidentally, in each administration step, it is preferable to set an interval between adjacent administration sites (puncture sites) to be 2 mm or more when a dose per site is 100 μL or less. As a result, it is possible to avoid influence by the adjacent administration site when acquiring the myoelectric response caused by the drug solution administration and to perform highly accurate measurement.

When a plurality of drug solutions having different compositions are tested, an administration rate and a dose of the drug solution at each administration step are set to be the same. In addition, when a plurality of administration conditions are tested for the drug solution having the same composition, the drug solution is administered with one or both of the administration rate and the dose of the drug solution changed in each administration step.

The dose per site at the plurality of administration sites is preferably a range of 10 to 100 μL in consideration of a planta pedis size of the rat 12. In addition, the total dose to the rat 12 at the plurality of administration sites is preferably a range of 200 μL or less. Examples of a combination of the dose and the number of administration sites may include 20 μL×8 sites (=160 μL), 50 μL×4 sites (=200 μL), 100 μL×2 sites (200 μL), and the like. In addition, the administration rate of the drug solution is a range of, for example, 5 to 100 μL/sec.

Incidentally, when the drug solution is administered only when the myoelectric response caused by the puncture occurs in the puncture step, it is possible to avoid wasteful drug solution administration. That is, when the myoelectric response is not observed despite the puncture, it is possible to prevent administration of the drug solution to a site where no myoelectric response occurs beforehand by piercing another site again.

The myoelectric potential generated in the semitendinosus muscle 12*b* of the rat 12 accompanying the injection (puncture and drug solution administration) is detected by the measurement electrode 24, and amplified by the high-sensitivity bioelectric amplifier 28, and then, sent to the data collection device 30. The myoelectric potential waveform is generated based on the myoelectric potential data by the data collection device 30. The generated myoelectric potential waveform is displayed on the monitor screen 32*a* of the personal computer 32.

Figure 2:
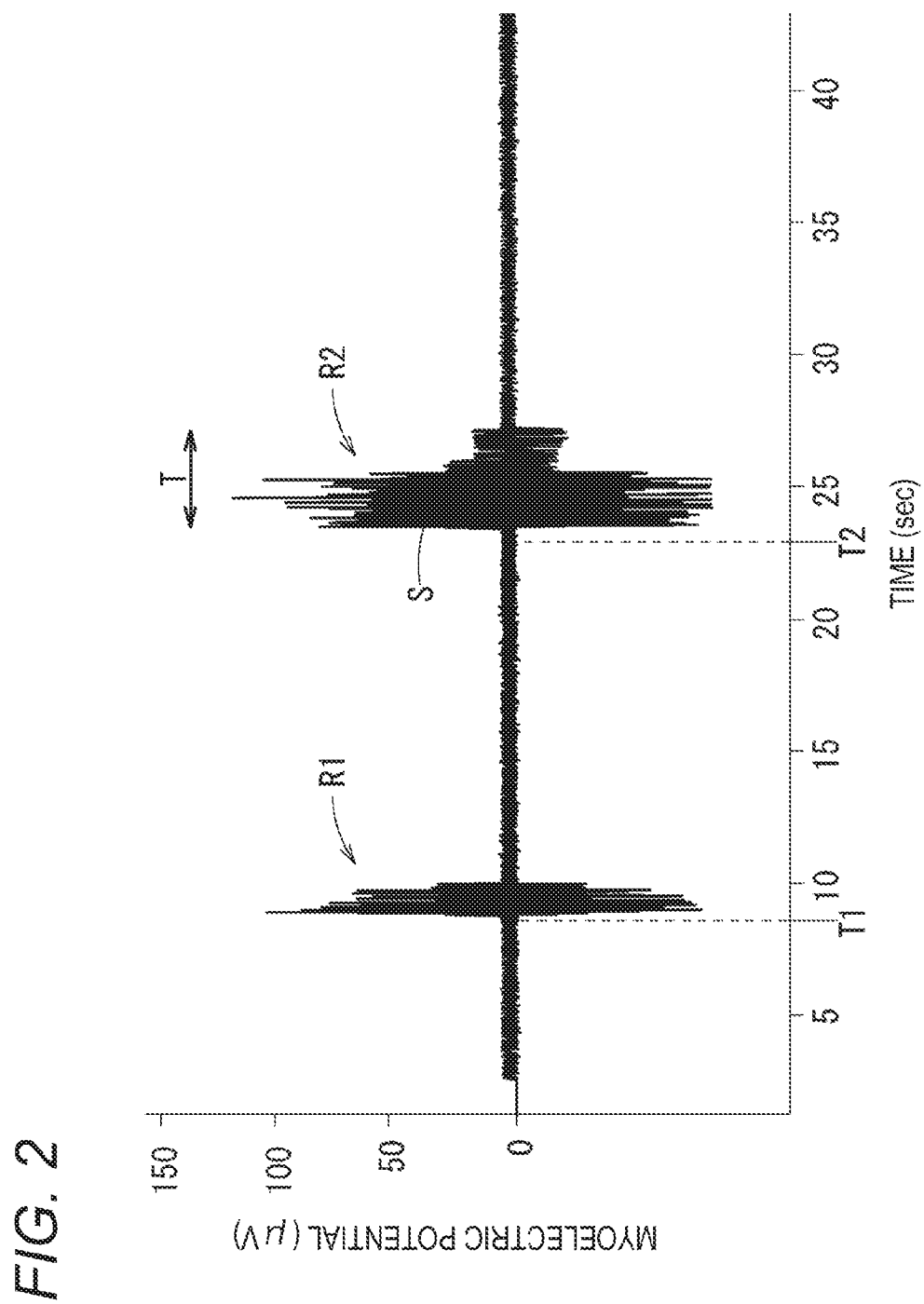
FIG. 2 is an example of a myoelectric potential waveform obtained by the method of the present invention.

FIG. 2 illustrates an example of the myoelectric potential waveform thus obtained. In FIG. 2, T1 is a time at which the injection needle 18 is punctured, and a myoelectric response (R1) caused by the puncture can be confirmed. In addition, T2 is a time when the administration of the drug solution to the rat 12 is started, and a myoelectric response (R2) caused by the drug solution administration can be confirmed.

As described above, the drug solution is administered to the anesthetized rat 12 through the injection needle 18 after the myoelectric response caused by the puncture of the injection needle 18 disappears in the present invention, and thus, the myoelectric response caused by the puncture and the myoelectric response caused by the drug solution administration do not overlap each other in time. That is, the myoelectric response caused by the drug solution administration can be measured separately from the myoelectric response caused by the puncture.

Once such a myoelectric potential waveform is obtained, the measurement step is performed in order to assess (quantify) the pain caused by the drug solution administration. In the measurement step, at least one of measurement of a duration time T of the myoelectric response caused by the drug solution administration and measurement of an integral value S obtained by integrating absolute values of myoelectric potentials during a period from the occurrence of the myoelectric response by the administration of the drug solution to the disappearance of the myoelectric response, that is, an EMG intensity (pV·s) is performed. The integral value S is the area of the myoelectric potential waveform obtained by rectifying the myoelectric potentials during the period of the duration time T of the myoelectric response and integrating the rectified values. The duration time T and the integral value S of the myoelectric response caused by the drug solution administration may be calculated by the personal computer 32, and a value calculated by the data collection device 30 may be displayed on the monitor screen 32*a*.

In this manner, according to the method of the present invention, the drug solution is administered to the rat 12 and the myoelectric response caused by the administration of the drug solution is measured after the myoelectric response caused by the puncture of the injection needle 18 disappears, and thus, the myoelectric response caused by the puncture and the myoelectric response caused by the drug solution administration do not overlap each other on the electromyogram (EMG). In this manner, it is possible to assess (quantify) the pain caused by the administration of the drug solution separately from the pain caused by the puncture. In this case, when the administration of the drug solution is started after a lapse of one second or more (more preferably 10 seconds or more) after the disappearance of the myoelectric response by the puncture, it is possible to effectively measure the myoelectric response caused by the drug solution administration separately from the myoelectric response caused by the puncture.

As described above, the puncture step, the administration step, and the measurement step are performed for each of the plurality of drug solutions having different compositions or for each of the plurality of administration conditions, and then, a drug solution composition with which the duration time T is shortest or the integral value S is smallest is identified among the plurality of drug solutions having different compositions, or an administration condition with which the duration time T is shortest or the integral value S is smallest is identified among the plurality of administration conditions (a identifying step). As a result, it is possible to select the drug solution composition or the administration condition accompanied by less pain.

Figure 3A:
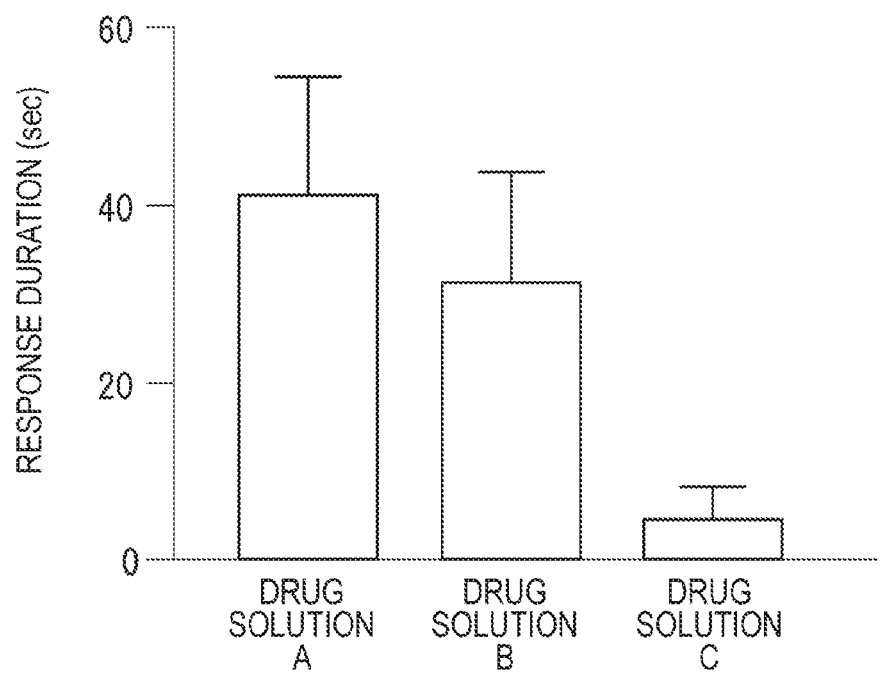
FIG. 3A is a graph illustrating a duration time of a myoelectric response caused by administration of each drug solution when a plurality of drug solutions having different compositions was injected into a rat.
Figure 3B:
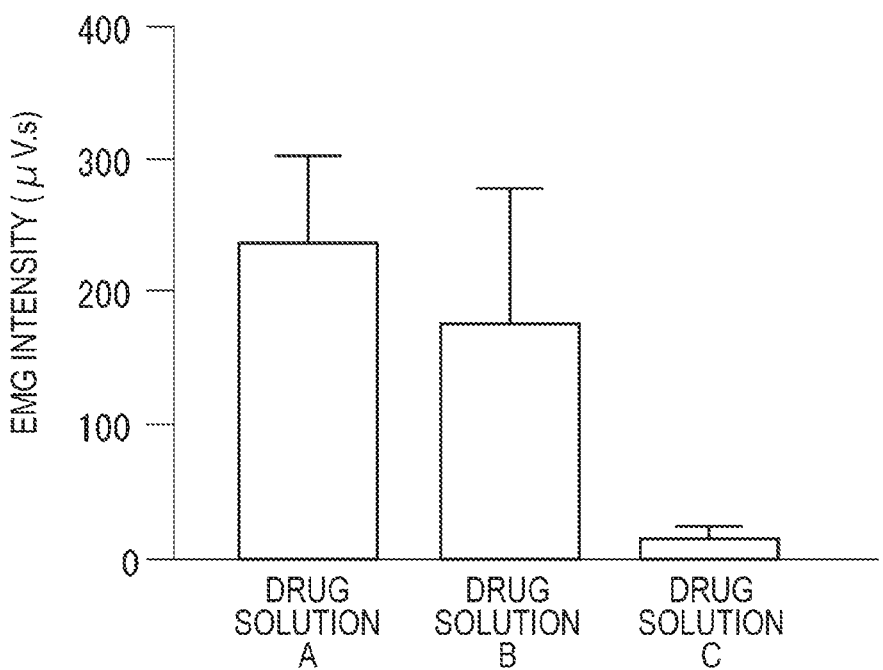
FIG. 3B is a graph illustrating the EMG intensity obtained from a myoelectric response caused by administration of each drug solution when the plurality of drug solutions having different compositions was injected into the rat.

FIG. 3A is a graph illustrating a duration time of a myoelectric response caused by administration of each drug solution when the plurality of drug solutions having different compositions was injected into a rat. FIG. 3B is a graph illustrating the EMG intensity obtained from a myoelectric response caused by administration of each drug solution when the plurality of drug solutions having different compositions was injected into the rat. From FIGS. 3A and 3B, it can be understood that the duration time of the myoelectric response and the EMG intensity differ depending on the drug solution composition regarding the rat, that is, there is a difference in pain caused by drug solution administration.

Figure 4A:
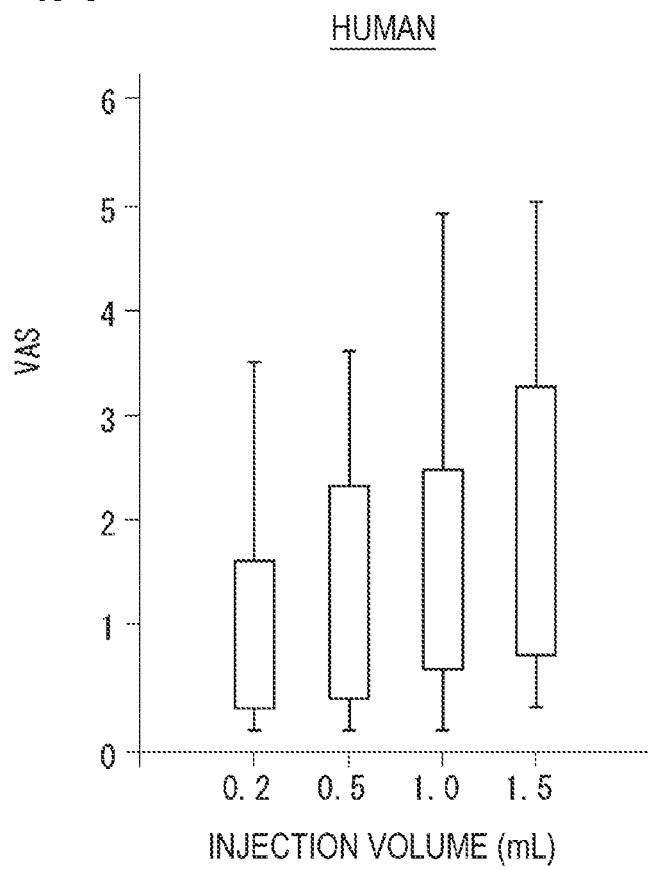
FIG. 4A is a graph illustrating the magnitude of pain (VAS) when a physiological saline was injected into a human at a plurality of different injection volume.
Figure 4B:
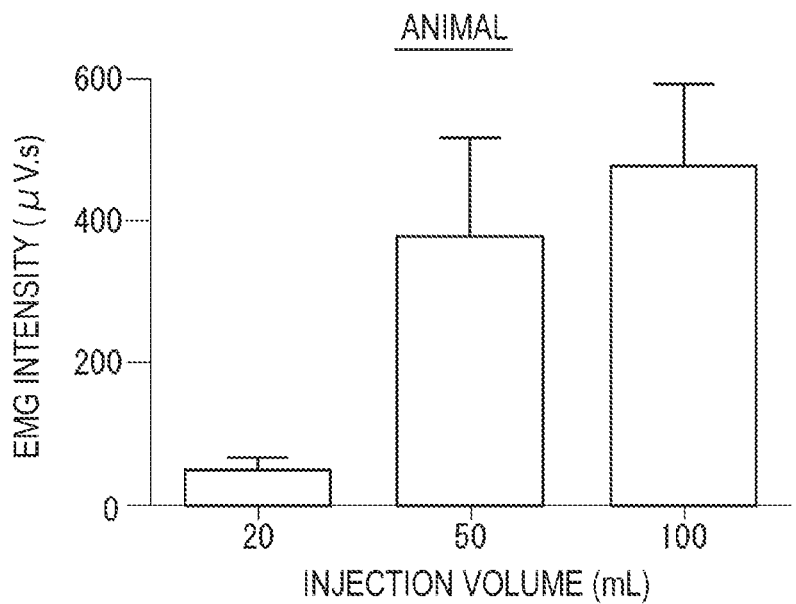
FIG. 4B is a graph illustrating the EMG intensity obtained from a myoelectric response caused by an injection solution when the physiological saline was injected into a rat at the plurality of different doses.

FIG. 4A is a graph illustrating the magnitude (VAS: visual analog scale) of pain when a physiological saline was injected into a human at a plurality of different doses (the source is illustrated at the lower part). The VAS is an assessment scale indicating a degree of current pain with a maximum of 10. FIG. 4B is a graph illustrating the EMG intensity obtained from a myoelectric response caused by an injection solution when a physiological saline was injected into a rat at the plurality of different doses From FIGS. 4A and 4B, it can be understood that both the human and the rat have the same tendency that the pain increases as the dose increases.

Figure 5A:
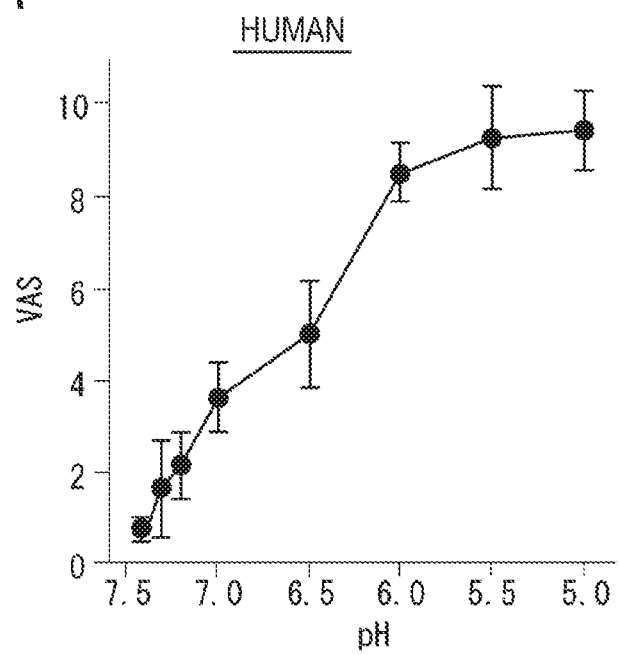
FIG. 5A is a graph illustrating the magnitude of pain (VAS) at the time of injection into a human with a plurality of different pH values.
Figure 5B:
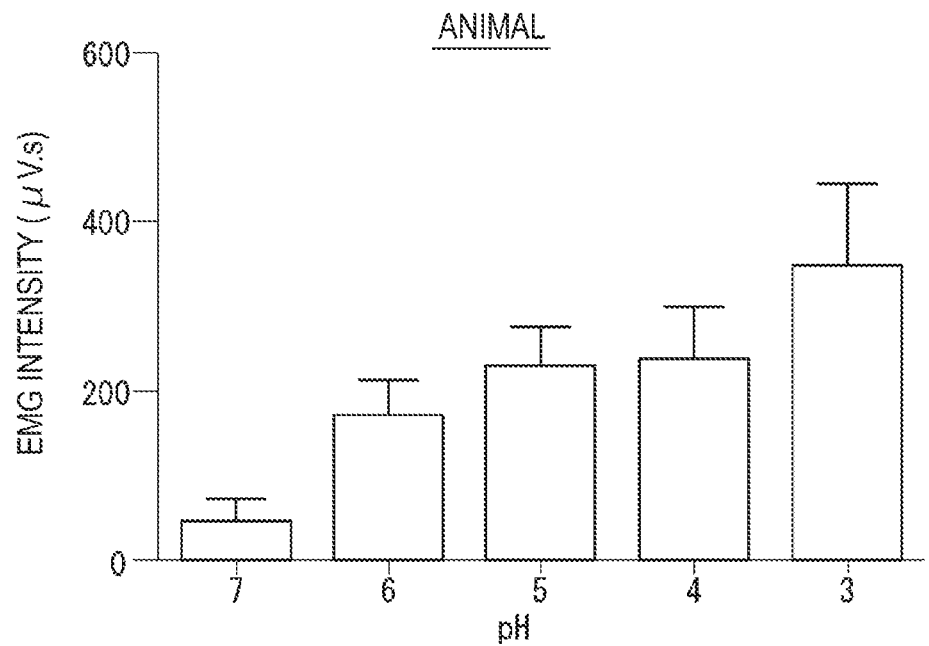
FIG. 5B is a graph illustrating the EMG intensity obtained from a myoelectric response caused by an injection solution at the time of injection into a rat with the plurality of different pH values.

FIG. 5A is a graph illustrating the magnitude of pain (VAS) at the time of injection into a human with a plurality of different pH values (the source is illustrated at the lower part). FIG. 5B is a graph illustrating the EMG intensity obtained from a myoelectric response caused by an injection solution at the time of injection into a rat with the plurality of different pH values. From FIGS. 5A and 5B, it can be understood that both the human and the rat have the same tendency that the pain increases as the pH value decreases.

Figure 6A:
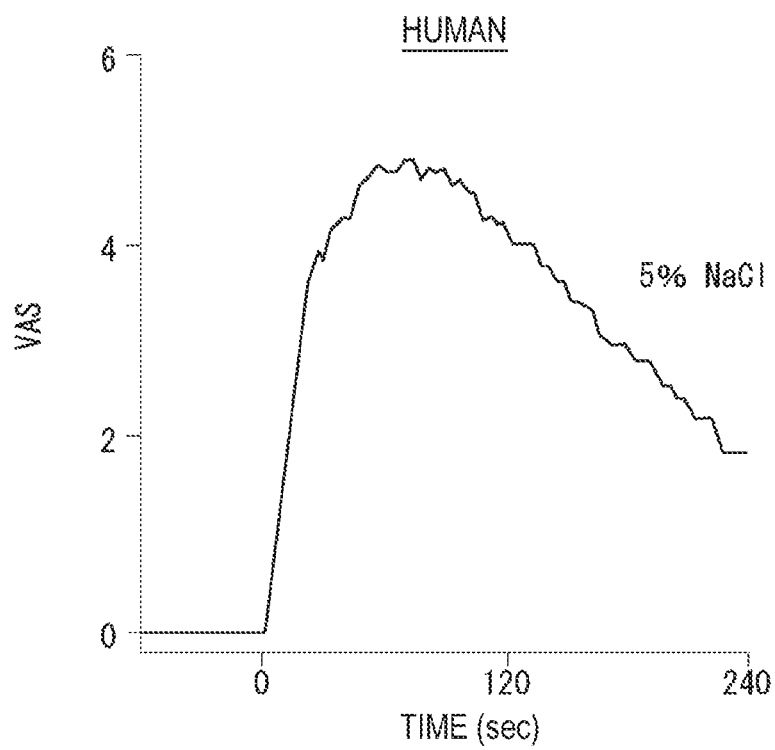
FIG. 6A is a graph illustrating the magnitude of pain (VAS) over time when 5% NaCl was injected into a human.
Figure 6B:
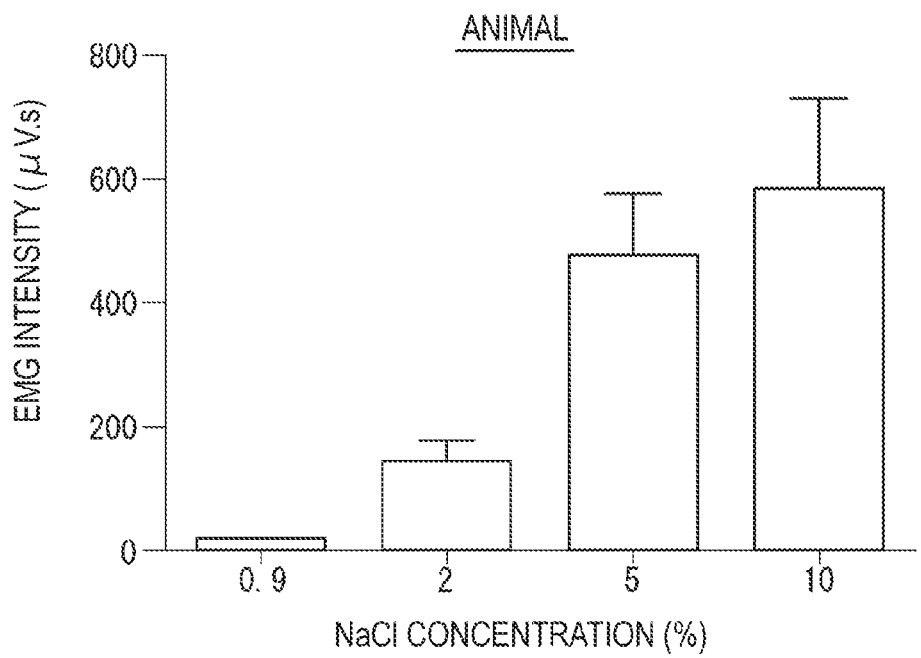
FIG. 6B is a graph illustrating the EMG intensity obtained from a myoelectric response caused by an injection solution when the NaCl was injected into a rat at a plurality of different concentrations.

FIG. 6A is a graph illustrating the magnitude of pain (VAS) over time when 5% NaCl was injected into a human (the source is illustrated at the lower part). From FIG. 6A, it can be understood that a great pain is caused when 5% NaCl is injected into the human. On the other hand, FIG. 6B is a graph illustrating the EMG intensity obtained from the myoelectric response caused by an injection solution when the NaCl was injected into a rat at a plurality of different concentrations. From FIG. 6B, it can be understood that the pain of the rat significantly increases when the NaCl concentration is 5% or more. Therefore, it can be understood from FIGS. 6A and 6B that the human and the rat indicate the same tendency with respect to the pain depending on the NaCl concentration.

Figure 7A:
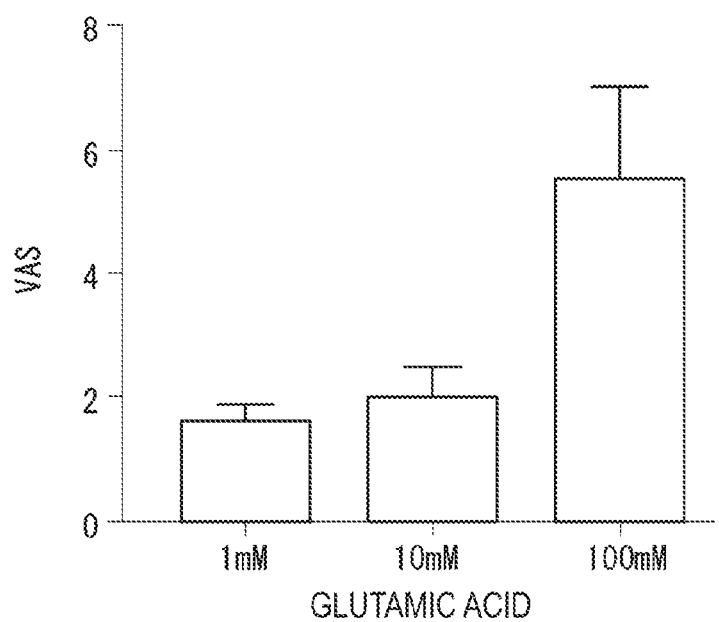
FIG. 7A is a graph illustrating the magnitude of pain (VAS) when glutamic acid was injected into a human at a plurality of different molar concentrations.
Figure 7B:
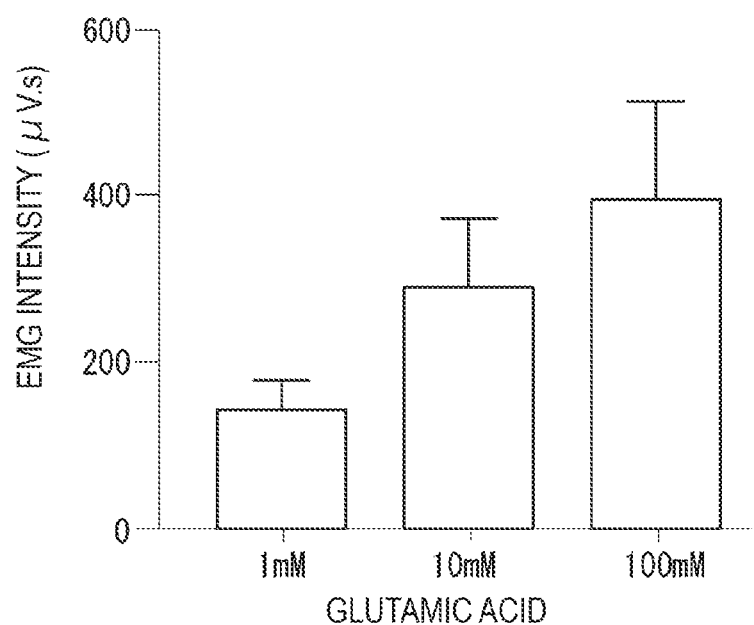
FIG. 7B is a graph illustrating the EMG intensity obtained from a myoelectric response caused by an injection solution when the glutamic acid was injected into a rat at the plurality of different molar concentrations.

FIG. 7A is a graph illustrating the magnitude of pain (VAS) when glutamic acid was injected into a human at a plurality of different molar concentrations. Incidentally, FIG. 7A is the graph created based on the source graph illustrated at the lower part of the drawing. FIG. 7B is a graph illustrating the EMG intensity obtained from a myoelectric response caused by an injection solution when glutamic acid was injected into a rat at the plurality of different molar concentrations. From FIGS. 7A and 7B, it can be understood that both the human and the rat have the same tendency that the pain increases as the molar concentration of glutamic acid increases.

As above, it can be understood that the magnitude of pain felt by the human indicates the same tendency as the measurement result of the myoelectric response using the rat. In addition, in the case of a mammal other than the rat, it can be considered that the mammal indicates the same tendency as the rat. Accordingly, the method of the present invention can be applied to development of a drug solution for humans, and an administration method.

Figure 8A:
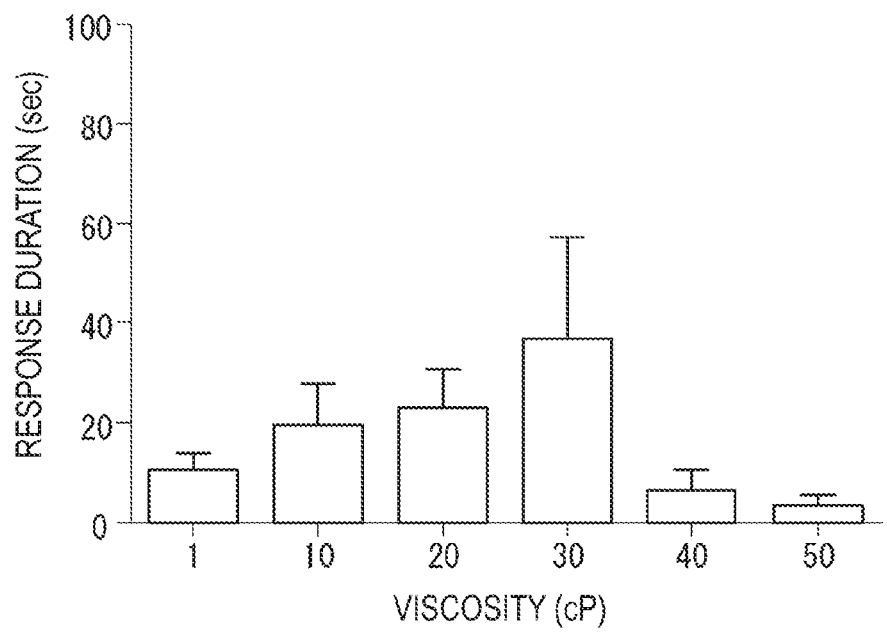
FIG. 8A is a graph illustrating a duration time of a myoelectric response caused by an injection solution when a polyethylene glycol/physiological saline mixed solution was injected into a rat at a plurality of different viscosities.
Figure 8B:
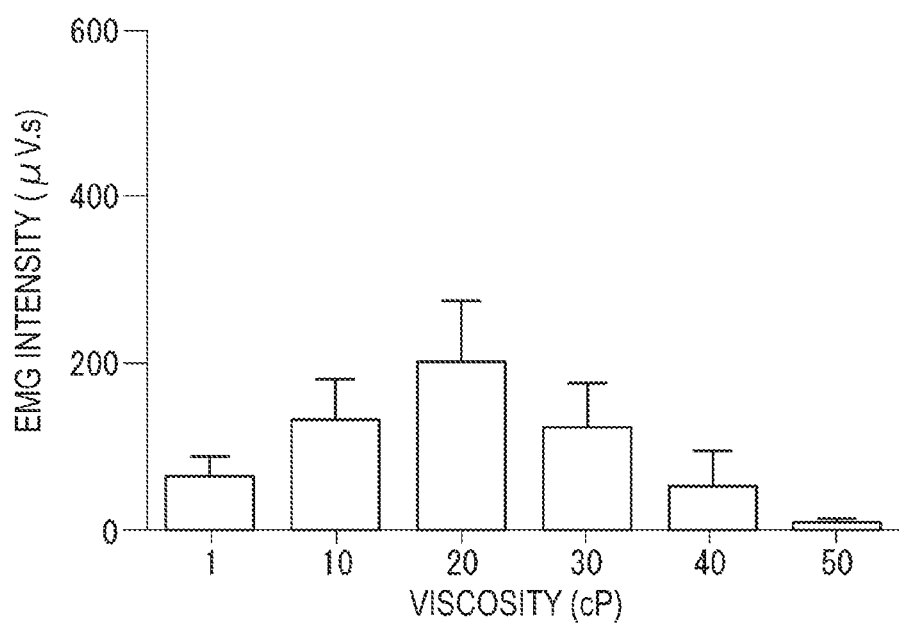
FIG. 8B is a graph illustrating the EMG intensity obtained from a myoelectric response caused by an injection solution when the polyethylene glycol/physiological saline mixed solution was injected into a rat with the plurality of different viscosities.

FIG. 8A is a graph illustrating a duration time of a myoelectric response caused by an injection solution when a polyethylene glycol/physiological saline mixed solution was injected into a rat at a plurality of different viscosities. FIG. 8B is a graph illustrating the EMG intensity obtained from a myoelectric response caused by an injection solution when the polyethylene glycol/physiological saline mixed solution was injected into a rat with the plurality of different viscosities. From FIGS. 8A and 8B, it can be understood that the magnitude of pain varies depending on the viscosity of the injection solution.

Figure 9A:
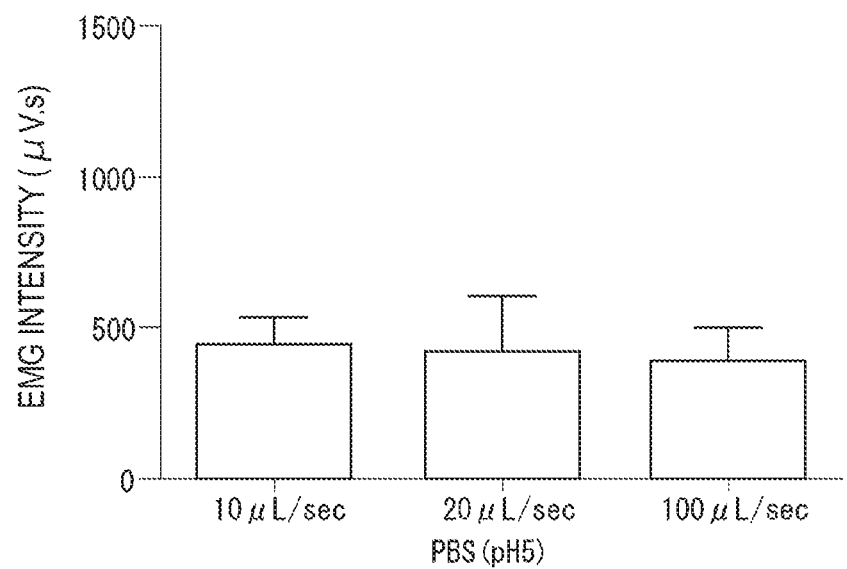
FIG. 9A is a graph illustrating the EMG intensity obtained from a myoelectric response caused by an injection solution when a phosphate buffered saline (pH 5) was injected into a rat at a plurality of different administration rates.
Figure 9B:
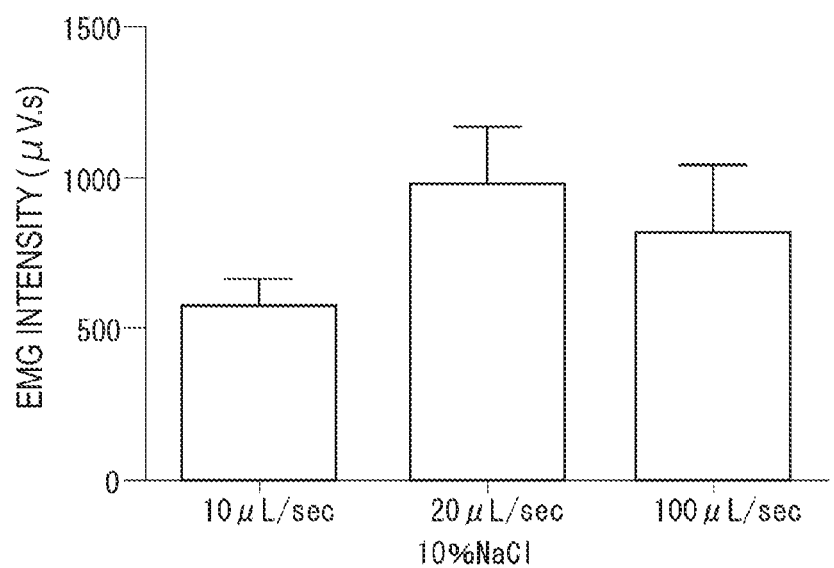
FIG. 9B is a graph illustrating the EMG intensity obtained from a myoelectric response caused by an injection solution when 10% NaCl was injected into a rat at a plurality of different administration rates.

FIG. 9A is a graph illustrating the EMG intensity obtained from a myoelectric response caused by an injection solution when a phosphate buffered saline (pH 5) was injected into a rat at a plurality of different administration rate. FIG. 9B is a graph illustrating the EMG intensity obtained from a myoelectric response caused by an injection solution when 10% NaCl was injected into a rat at a plurality of different administration rates. From FIGS. 9A and 9B, it can be understood that the magnitude of pain varies depending on a difference in the administration rate of the injection solution depending on the composition of the injection solution.

Next, specific examples of assessment of the pain caused by the drug solution administration using the rat 12 will be described. In this example, drug solutions of Samples 1 to 3 having different compositions (an injectable aqueous preparation for inflammatory autoimmune disease treatment) were prepared as follows.

(Sample 1)

Disodium hydrogenphosphate (anhydrous) of 0.71 g was dissolved in water for injection of 50 mL. Sodium dihydrogen phosphate (anhydrous) of 0.60 g was dissolved in water for injection of 50 mL. A mixture was obtained with a volume ratio of the disodium hydrogenphosphate solution: the sodium dihydrogen phosphate solution=87:13, and the mixture was diluted to 1/10 in concentration with water for injection to prepare a 10 mM phosphate buffer solution. Methotrexate of 125 mg and sodium chloride of 27 mg were dissolved in the 10 mM phosphate buffer solution of 5 mL, and the pH thereof was adjusted to around 7.5 with an appropriate amount of sodium hydroxide, thereby obtaining an aqueous solution having a methotrexate concentration of 25 mg/mL. This aqueous solution was filtered using a membrane filter having a pore diameter of 0.2 μm to prepare the injectable aqueous preparation for inflammatory autoimmune disease treatment.

(Sample 2)

An injectable aqueous preparation containing methotrexate at pH 8.0 was prepared in the same manner as Sample 1, except that an added amount of sodium hydroxide in Sample 1 was changed.

(Sample 3)

An injectable aqueous preparation containing methotrexate at pH 8.5 was prepared in the same manner as Sample 1, except that an added amount of sodium hydroxide in Sample 1 was changed.

The measurement system 10 illustrated in FIG. 1 was used to measure an electromyogram (EMG) when the injectable aqueous preparations containing methotrexate of Samples 1 to 3 were administered to the rat 12.

Specifically, the rat 12 was anesthetized with isoflurane at a concentration of 3%/Air and the semitendinosus muscle 12b was exposed. The anesthesia was lowered to about 1.5%/Air, and the clip-type stimulating electrode 34 was attached to distal ends of toes. An electrical stimulus (40 Hz, 10 mA, 2 ms) was applied, and the measurement electrode 24 was inserted into a position where contraction was observed. The electrical stimulus intensity was lowered to 5 mA, and the anesthetic concentration was lowered (a range of 1 to 1.4%/Air) until obtaining a response of about 100 μV. The rat 12 is stabilized for 30 minutes or more after the change of the anesthetic concentration, and then, the drug solution was administered to the rat 12.

During the administration of the drug solution to the rat 12, the syringe 14 of 1 mL was loaded in the syringe pump 20, the injection needle 18 of 29 G was punctured under the plantar subcutaneous 12a, and the drug solution of 20 μL was administered at an administration rate of 10 μL/sec. Samples 1 to 3 were sequentially administered to the rat 12 under the same administration conditions. Measurement results of the EMG intensity is illustrated in FIG. 10.

Figure 10:
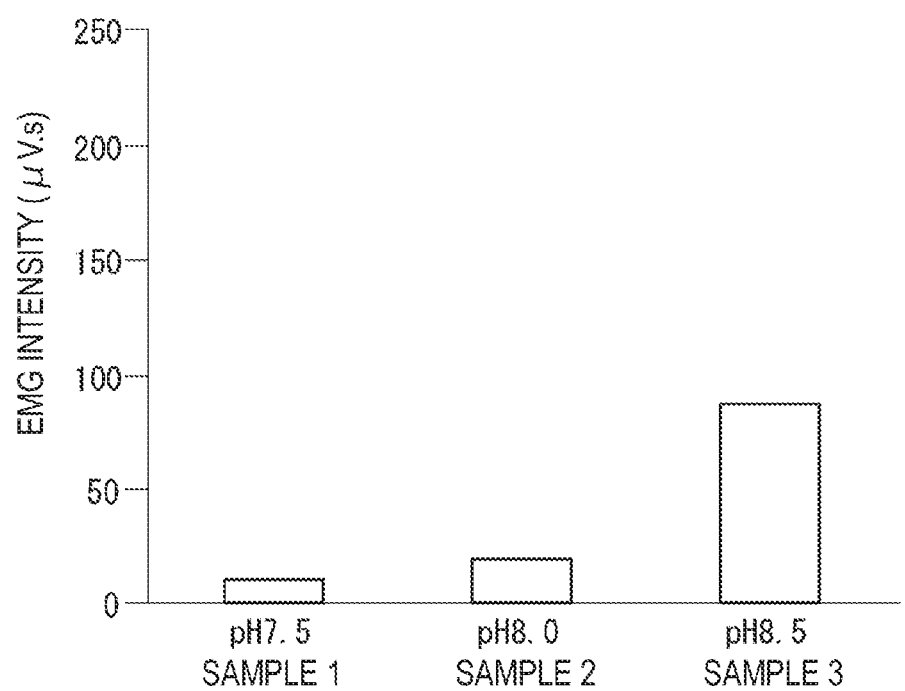
FIG. 10 is a graph illustrating examples of the present invention, and is the graph illustrating the EMG intensity obtained from a myoelectric response caused by drug solution administration when a plurality of drug solutions having different pHs (an injectable aqueous preparation for inflammatory autoimmune disease treatment) was injected into a rat.

From FIG. 10, it was found that the EMG intensity caused by drug solution administration of Sample 1 was smallest among Samples 1 to 3 having different compositions. That is, it was found that the pain caused by the drug solution administration of Sample 1 was the least. Therefore, in the present embodiment, it was determined to select the drug solution composition of Sample 1 as the injectable aqueous preparation for inflammatory autoimmune disease treatment accompanied by less pain.

Although embodiments of the present invention have been described with above, the present invention is not limited to the above-described embodiments, and various modifications can be made within a scope that does not depart from a gist of the present invention.

FIG. 1
30 DATA COLLECTION DEVICE
28 AMPLIFIER
FIG. 2
MYOELECTRIC POTENTIAL (μV)
TIME (sec)
FIG. 3A
RESPONSE DURATION (sec)
DRUG SOLUTION A
DRUG SOLUTION B
DRUG SOLUTION C
FIG. 3B
EMG INTENSITY (μV·s)
DRUG SOLUTION A
DRUG SOLUTION B
DRUG SOLUTION C
FIG. 4A
HUMAN
INJECTION VOLUME (mL)
FIG. 4B
ANIMAL
EMG INTENSITY (μV·s)
INJECTION VOLUME (mL)
FIG. 5A
HUMAN
FIG. 5B
ANIMAL
EMG INTENSITY (μV·s)
FIG. 6A
HUMAN
TIME (sec)
FIG. 6B
ANIMAL
EMG INTENSITY (μV·s)
NaCl CONCENTRATION (%)
FIG. 7A
HUMAN
GLUTAMIC ACID
FIG. 7B
ANIMAL
EMG INTENSITY (μV·s)
GLUTAMIC ACID
FIG. 8A
RESPONSE DURATION (sec)
VISCOSITY (cP)
FIG. 8B
EMG INTENSITY
VISCOSITY
FIG. 9A
EMG INTENSITY (μV·s)
FIG. 9B
EMG INTENSITY (μV·s)
FIG. 10
EMG INTENSITY (μV·s)
SAMPLE 1
SAMPLE 2
SAMPLE 3

What is claimed is:

1. A method for assessing pain caused by administration of a drug solution, the method comprising:
   preparing a mammalian experimental animal having a plantar subcutaneous tissue, and a semitendinous muscle bent by a spinal reflex when a stimulus is applied to the plantar subcutaneous tissue;
   anesthetizing the experimental animal by inhalation anesthesia;
   inserting a measurement electrode into the semitendinous muscle of the anesthetized experimental animal;
   puncturing a plurality of injection needles into a plurality of administration sites in the plantar subcutaneous tissue of the anesthetized experimental animal while measuring a myoelectric potential of the semitendinous muscle with the measurement electrode and leaving the plurality of needles in place until after at least one drug solution has been administered;
   administering at least one drug solution to the anesthetized experimental animal through the plurality of injection needles after a myoelectric response caused by the puncture of the injection needles disappears, which comprises (i) administering a plurality of drug solutions having different compositions to the plurality of administration sites under identical administration conditions, or (ii) administering a single drug solution to the plurality of administration sites under different administration conditions; and
   performing at least one of: (i) measurement of a duration time of the myoelectric response caused by the administration of the drug solution, and (ii) measurement of an EMG intensity obtained by integrating absolute values of myoelectric potentials during a period from occurrence of the myoelectric response by the administration of the at least one drug solution to disappearance of the myoelectric response.

2. The method according to claim 1, wherein the step of administering comprises:
   administering the plurality of drug solutions having different compositions to the plurality of administration sites under identical administration conditions.

3. The method according to claim 1, wherein the step of administering comprises:
   administering the single drug solution to the plurality of administration sites under different administration conditions.
4. The method according to claim 2, wherein:
   the experimental animal is a rat.
5. The method according to claim 3, wherein:
   the experimental animal is a rat.
6. The method according to claim 4, wherein:
   a dose per site at the plurality of administration sites is a range of 10 to 100 μL.
7. The method according to claim 5, wherein:
   a dose per site at the plurality of administration sites is a range of 10 to 100 μL.
8. The method according to claim 6, wherein:
   an interval between the administration sites, adjacent to each other, is set to be 2 mm or more.
9. The method according to claim 7, wherein:
   an interval between the administration sites, adjacent to each other, is set to be 2 mm or more.
10. The method according to claim 3, wherein:
    a total dose at the plurality of administration sites is 200 μL or less.
11. The method according to claim 4, wherein:
    an administration rate of the drug solution is a range of 5 to 100 μL/sec.
12. The method according to claim 5, wherein:
    an administration rate of the drug solution is a range of 5 to 100 μL/sec.
13. The method according to claim 2, wherein:
    the administration of the drug solution is started after a lapse of one second or more from when the myoelectric response caused by the puncture has disappeared.
14. The method according to claim 3, wherein:
    the administration of the drug solution is started after a lapse of one second or more from when the myoelectric response caused by the puncture has disappeared.
15. The method according to claim 1, wherein:
    the drug solution is administered only when the myoelectric response caused by the puncture occurs.
16. The method according to claim 1, wherein:
    the measurement electrode is a bipolar electrode, and a reference electrode is pasted to a thoracic skin surface of the experimental animal.
17. A method for selecting drug solution administration, the method comprising:
    a preparation step comprising preparing a mammalian experimental animal having a plantar subcutaneous tissue, and a semitendinous muscle bent by a spinal reflex when a stimulus is applied to the plantar subcutaneous tissue;
    an anesthesia step comprising anesthetizing the experimental animal by inhalation anesthesia;
    a measurement electrode placement step comprising placing a measurement electrode in the semitendinous muscle of the anesthetized experimental animal;
    a puncture step comprising puncturing a plurality of injection needles into a plurality of administration sites in the plantar subcutaneous tissue of the anesthetized experimental animal while measuring a myoelectric potential of the semitendinous muscle by the measurement electrode and leaving the plurality of needles in place until after at least one drug solution has been administered;
    an administration step comprising administering at least one drug solution to the anesthetized experimental animal through the plurality of injection needles after a myoelectric response caused by the puncture of the injection needles disappears, which comprises (i) administering a plurality of drug solutions having different compositions to the plurality of administration sites under identical administration conditions, or (ii) administering a single drug solution to the plurality of administration sites under different administration conditions; and
    a measurement step of performing at least one of (i) measurement of an EMG intensity obtained by integrating absolute values of the myoelectric potential from occurrence to disappearance of the myoelectric response caused by the administration of the drug solution, and (ii) measurement of a duration time of the myoelectric response caused by the administration of the drug solution,
    wherein the puncture step, the administration step, and the measurement step are performed for each of a plurality of drug solutions having different compositions or for each of a plurality of administration conditions, and
    wherein the method further comprises at least one of (i) an identifying step comprising identifying a drug solution composition with which the duration time is shortest or the EMG intensity is smallest, among the plurality of drug solutions having different compositions, or (ii) identifying an administration condition with which the duration time is shortest or the EMG intensity is smallest, among the plurality of administration conditions.

* * * * *